United States Patent [19]

Hall et al.

[11] Patent Number: 5,374,724
[45] Date of Patent: Dec. 20, 1994

[54] PROCESS FOR THE PREPARATION OF SUBSTITUTED ACETIC ACIDS

[75] Inventors: Nigel Hall, Bury; Nigel Hughes, Oldham; Prakash Patel, Huddersfield, all of England

[73] Assignee: Zeneca, Limited, London, England

[21] Appl. No.: 970,189

[22] Filed: Nov. 2, 1992

Related U.S. Application Data

[62] Division of Ser. No. 817,615, Jan. 7, 1992, Pat. No. 5,189,181.

[30] Foreign Application Priority Data

Jan. 8, 1991 [GB] United Kingdom ............... 9100303
May 23, 1991 [GB] United Kingdom ............... 9111144

[51] Int. Cl.$^5$ ............... C07D 413/00; C07D 215/12; C07D 277/04; C07D 333/32
[52] U.S. Cl. ............... 544/111; 544/128; 544/129; 544/146; 544/148; 544/165; 544/166; 546/165; 546/174; 546/187; 546/190; 546/191; 546/193; 546/194; 546/201; 546/208; 546/212; 546/213; 546/229; 546/235; 546/238; 546/256; 546/264; 546/267; 546/284; 546/329; 546/333; 546/335; 549/59; 549/65; 549/66; 562/441
[58] Field of Search ............... 562/441, 457, 458, 461; 549/45, 47, 299, 59, 65, 66; 546/197, 165, 174, 187, 190, 191, 193, 194, 201, 280, 212, 213, 229, 235, 238, 256, 264, 267, 284, 329, 333, 338; 544/148, 111, 128, 129, 146, 165, 166; 534/725

[56] References Cited

U.S. PATENT DOCUMENTS

| 2,756,254 | 7/1956 | Kesslin | 562/491 |
| 3,038,935 | 6/1962 | Gerber et al. | 562/468 |
| 3,499,008 | 3/1970 | Talet et al. | 562/468 X |
| 3,703,597 | 11/1972 | Rothweiler | 562/468 |
| 3,766,260 | 10/1973 | Carney et al. | 562/441 |
| 3,786,085 | 1/1974 | Dickel et al. | 562/441 X |
| 4,115,404 | 9/1978 | Greenhalgh et al. | 549/299 |
| 4,333,887 | 6/1982 | Carey et al. | 549/299 X |
| 4,650,882 | 3/1987 | Kenyon et al. | 549/299 |
| 4,680,417 | 7/1987 | Kenyon et al. | 549/299 |
| 5,077,416 | 12/1991 | Ueda et al. | 549/299 |
| 5,084,580 | 1/1992 | Kenyon et al. | 549/299 |
| 5,189,181 | 2/1993 | Hall et al. | 50/441 |

FOREIGN PATENT DOCUMENTS

| 0033583 | 8/1981 | European Pat. Off. | 549/299 |
| 0252406 | 1/1988 | European Pat. Off. | 549/299 |
| 0363034 | 4/1990 | European Pat. Off. | 549/299 |
| 1258677 | 10/1989 | Japan | 549/299 |
| 2103231 | 2/1983 | United Kingdom | 549/299 |

OTHER PUBLICATIONS

Farrell et al, "The Formation of Malonotrile Derivatives in the Reaction of Tetracyanoethylene with NN--Dialkylanilines", J. Chem. Soc., (C), pp. 1394–1396 (1970).
Fuerstenwerth et al, Chemical Abstracts, vol. 108, No. 152148r (1988).
Kenyon et al, Chemical Abstracts, vol. 165, No. 192863q (1986).
Greenhalgh et al, Chemical Abstracts, vol. 87, No. 186078f (1977).
Greenhalgh et al, Chemical Abstracts, vol. 95, No. 221293m (1981).
Greenhalgh et al, Chemical Abstracts, vol. 94, No. 104878z (1981).
Kenyon et al VI, Chemical Abstracts, vol. 104, No. 70385m (1986).

Primary Examiner—C. Warren Ivy
Assistant Examiner—Raymond Covington
Attorney, Agent, or Firm—Cushman, Darby & Cushman

[57] ABSTRACT

A process for the preparation of a substituted acetic acid of the Formula (2):

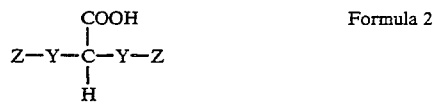

Formula 2 wherein
—X—Z is an optionally substituted aromatic or heteroaromatic optionally substituted amino radical; by reacting a compound of the Formula (7):

Z—Y—H    Formula 7 with glyoxylic acid. The compounds of Formula (2) are useful as intermediates in the preparation of polycyclic dyes.

1 Claim, No Drawings

PROCESS FOR THE PREPARATION OF SUBSTITUTED ACETIC ACIDS

This is a division of application Ser. No. 07/817,615, filed, Jan. 7,1992 now U.S. Pat. No. 5,189,181.

This specification describes an invention relating to a process for the preparation of certain polycyclic dyes. According to the present invention there is provided a process for the preparation of a polycyclic dye of the Formula (1):

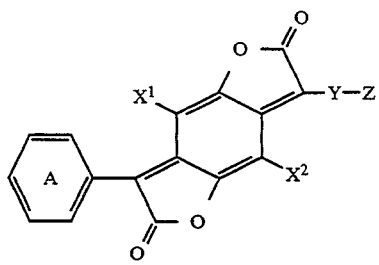

Formula 1 by reacting a substituted acetic acid of the Formula (2):

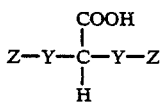

Formula 2 with a compound of the Formula (3):

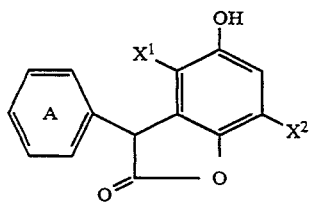

Formula 3 and oxidation of the intermediate leuco compound to dehydrogenate the peripheral heterocyclic rings wherein Y is an optionally substituted aromatic or heteroaromatic radical;

Ring A is unsubstituted or is substituted by from one to five groups; Z is —$NR^1R^2$;

$R^1$ and $R^2$ are each independently H or are independently selected from optionally substituted alkyl, alkenyl, cycloalkyl, aralkyl, aryl and heteroaryl; or $R^1$ and $R^2$ together with the nitrogen atom to which they are attached form a heterocyclic ring; or $R^1$ and $R^2$ each independently together with the nitrogen to which they are attached and the adjacent carbon atom of Ring B form a heterocyclic ring; and $X^1$ and $X^2$ are each independently selected from H, halogen, optionally substituted alkyl, optionally substituted aryl, optionally substituted heteroaryl, cyano, carbamoyl, sulphamoyl, carboxylic acid and carboxylic acid ester.

The optionally substituted aromatic or heteroaromatic radical represented by Y is preferably selected from phenyl, pyridyl, naphthyl, thienyl, thiazolyl, isothiazolyl, benzothiazolyl, benzoisothiazolyl, imidazolyl, benzimidazolyl, indolyl, pyrazolyl, pyrimidyl and benzoxazolyl each of which may be substituted or unsubstituted. It is preferred that the optionally substituted aromatic or heteroaromatic radical represented by Y is a radical of the Formula (4):

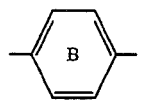

Formula 4 or a radical of the Formula (5):

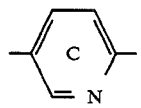

Formula 5 or a radical of the Formula (6):

Formula 6 wherein

Ring B is unsubstituted or is substituted by from one to four further groups;

Ring C is unsubstituted or is substituted by from one to three further groups;

Ring D is unsubstituted or is substituted by one or two further groups.

The alkyl groups represented by $R^1$, $R^2$, $X^1$ and $X^2$ are preferably straight or branched chain $C_{1-10}$-alkyl, more preferably $C_{1-6}$-alkyl and especially $C_{1-4}$-alkyl.

The alkenyl groups represented by $R^1$ and $R^2$ are preferably $C_{2-10}$-alkenyl and more preferably $C_{3-4}$-alkenyl especially alkyl.

The cycloalkyl groups represented by $R^1$ and $R^2$ are preferably $C_{4-8}$-cycloalkyl and more preferably cyclohexyl.

The aralkyl groups represented by $R^1$ and $R^2$ are preferably phenyl-$C_{1-4}$-alkyl, for example, benzyl or phenylethyl.

The aryl groups represented by $R^1$, $R^2$, $X^1$ and $X^2$ are preferably phenyl or naphthyl.

The heteroaryl groups represented by $R^1$, $R^2$, $X^1$ and $X^2$ are preferably pyridyl or thienyl.

The halogen groups represented by $X^1$ and $X^2$ are preferably fluoro, chloro and bromo.

The carbamoyl and sulphamoyl groups represented by $X^1$ and $X^2$ are preferably of the formula —$CONL^1L^2$ or —$SO\,NL^1L^2$ wherein $L^1$ and $L^2$ are each independently —H, $C_{1-4}$-alkyl, substituted $C_{1-4}$-alkyl or aryl, preferably phenyl or substituted phenyl.

The carboxylic ester groups represented by $X^1$ and $X^2$ are preferably of the formula —$COOL^3$ wherein $L^3$ is $C_{1-4}$-alkyl, substituted $C_{1-4}$-alkyl, or aryl, preferably phenyl or substituted phenyl.

Where the groups $R^1$ and $R^2$ together with the nitrogen to which they are attached form a heterocyclic ring this is preferably alicyclic for example piperidino or morpholino.

Where the groups $R^1$ and $R^2$ each independently together with the nitrogen to which they are attached and the adjacent carbon atom of the ring form a heterocyclic ring this is preferably alicyclic. Where one of $R^1$ and $R^2$ are involved thus together with Ring B form a tetrohydroquinolino nucleus. Where R¹ and R² are both involved a julolidino group is formed.

Where the groups R¹, R², X¹ and X² are optionally substituted examples of preferred substituents are $C_{1-4}$-alkyl, $C_{2-4}$-alkenyl, $C_{1-4}$-alkoxy, $C_{1-4}$-alkoxy-$C_{1-4}$-alkoxy, $C_{1-4}$-alkylcarbonyl, $C_{1-4}$-alkoxycarbonyl, $C_{1-4}$-alkoxy, $C_{1-4}$-alkxycarbonyl, $C_{1-4}$-alkylcarbonyloxy, $C_{1-4}$-alkoxycarbonyloxy, $C_{1-4}$-alkoxy-$C_{1-4}$-alkoxycarbonyloxy, $C_{1-4}$-alkoxycarbonyl-$C_{1-4}$-alkoxy, $C_{1-4}$-alkoxy-$C_{1-4}$-alkoxycarbonyl-$C_{1-4}$-alkoxy, $C_{1-4}$-alkylcarbonyloxy-$C_{1-4}$-alkoxy, cyano-$C_{1-4}$-alkoxy, hydroxy-$C_{1-4}$-alkoxy, $C_{1-4}$-alkylthio, phenylthio, $C_{4-8}$-cyclohexyl nitro, halogen, especially fluoro, chloro or bromo, phenyl, diphenyl, hydroxy, cyano, amino, $C_{1-4}$-alkylamino, di($C_{1-4}$-alkyl)amino.

Any of the substituents described above for R¹, R², X¹ and X² are suitable substituents for any of the Rings A, B, C and D. Ring A may also be substituted by the group Z defined above.

It is preferred that when Ring A is substituted by from 1-3 substituents that these occupy the 3-, 4- or 5-positions on Ring A; it is especially preferred that when Ring A is substituted by 1 or 2 substituents that these occupy the 4- position or the 3- and 4-positions.

It is preferred that Ring A is unsubstituted or is substituted by —NR¹R¹, $C_{1-4}$-alkyl $C_{1-4}$-alkoxy, halo and $C_{1-4}$-alkoxycarbonyl-$C_{1-4}$-alkoxy-$C_{1-4}$-alkoxy groups, where R¹ and R² are as hereinbefore defined.

It is preferred that apart from the group NR¹R² Ring B is unsubstituted or is substituted by 1 or 2 groups in the 3- or the 3- and 5-positions (i.e., ortho to the group NR¹R²) and preferred substituents are $C_{1-4}$-alkyl $C_{1-4}$-alkoxy and halo especially methyl, ethyl, isopropyl, methoxy, ethoxy and chloro.

It is preferred that X¹ and X² are both hydrogen.

It is preferred that Y is a phenylene group either unsubstituted or substituted by one or two methyl groups, or one or two ethyl groups, or one methyl and one ethyl group; it is preferred that these substituents are ortho to the group Z. It is preferred that the group Z is —NH₂ or —NHC₂H₅.

A preferred sub-group of dyes of Formula (1) is of Formula (8):

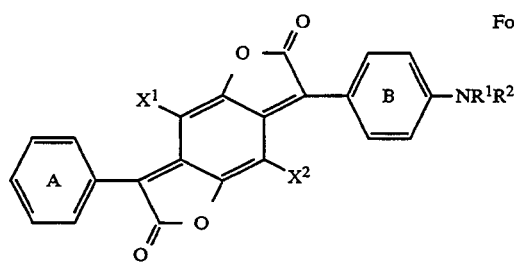

Formula 8 wherein:
Ring A is substituted by from 1 to 3 substituents selected from $C_{1-4}$-alkyl, $C_{1-4}$-alkoxy, halo, hydroxy and —NR¹R²;
Ring B is a phenylene group which is unsubstituted or substituted by from 1 to 2 substituents selected from $C_{1-4}$-alkyl, $C_{1-4}$-alkoxy and halogen;
R¹ and R² are each independently H or $C_{1-4}$-alkyl; and
X¹ and X² are H.

The present process maybe carried out by heating the reactants in a melt but preferably in a liquid medium and with a boiling point above 80° C. and especially from 80° C. to 210° C. especially in an organic liquid such as 1,2-dichlorobenzene, 1,2,4-trichlorobenzene, methoxybenzene, xylene, chlorobenzene or 1,3,5-trimethylbenzene. The present process may optionally be carried out in the presence of an acid catalyst. Suitable acid catalysts include acetic, sulphuric, phosphoric and p-toluene sulphonic acids.

The present process is preferably carried out at a temperature from 80° C. to 210° C., especially at a temperature from 130° C. to 180° C. Where an organic liquid is used as the liquid medium the reaction is conveniently carried out under reflux. The reaction may optionally be carried out in an autoclave, preferably at pressures from 1 to 30 bar and more preferably from 1 to 15 bar.

The reaction is continued until all the starting materials are consumed which can take up to 100 hours.

The oxidation of the intermediate leuco compound is achieved by use of any convenient oxidising agent for dehydrogenating a carbon-carbon single bond such as chloranil, benzoquinone, hydrogen peroxide or alkali metal, preferably sodium and potassium, perborates, percarbonates or persulphates. The oxidation step is preferably carried out at a temperature from 30° C. to 150° C., and more preferably at a temperature from 75° C. to 125° C.

When the reaction is essentially complete, preferably when substantially all the starting materials are consumed, the product may be isolated by any convenient means such as filtration. The product may be purified by any convenient means, for example, by washing with solvents, crystallisation or column chromatography According to a further feature of the invention there is provided a process for the preparation of a substituted acetic acid of the Formula (2):

Formula 2 wherein Y and Z are as hereinbefore defined; by reacting a compound of the Formula (7):

Formula 7 with glyoxylic acid.

This reaction is conveniently carried out in a liquid medium preferably in an organic solvent such as methanol, ethanol.

The reaction is preferably carried out at a temperature from −10° C. to 50° C., more preferably at a temperature from 15° C. to 25° C.

The reaction is continued until all starting materials are consumed which can take up to 30 hours. The product may be isolated by any convenient means such as filtration. The product may be purified by any convenient means for example by washing with water, washing with solvent or crystallisation.

According to a further feature of the present invention there is provided a compound of the Formula (2) wherein Y and Z are as hereinbefore defined.

Compounds of the Formula (3) may be conveniently prepared by reaction of a dihydroxybenzene with a mandelic acid derivative. EP 0033583 describes such a preparation in detail.

The invention is further illustrated by the following examples in which all parts are by weight:

EXAMPLE 1

A mixture of 6-ethyl-2-methylaniline (30.0 parts) and methanol (100 parts) was stirred at ambient temperature. Glyoxylic acid 50% w/v (16.5 parts) was added and the mixture was stirred for 24 hours at ambient temperature. The precipitated product was isolated by filtration, washed with methanol (20 parts) and dried to yield di(4-amino-5-ethyl-3-methylphenyl)acetic acid (31.0 parts).

EXAMPLE 2

A mixture of 5-hydroxy-2-oxo-3-phenyl-2,3-dihydrobenzofuran (3.5 parts), di(4-amino-5-ethyl-3-methylphenyl)acetic acid (5.0 parts) and 1,2-dichlorobenzene (50 parts) was stirred under reflux, under a stream of nitrogen for 48 hours. After cooling to 100° C., chloranil (1.8 parts) was added and the mixture was allowed to stir and cool to ambient temperature. Petroleum ether (30 parts) was added, the mixture was stirred for 1 hour and the product was isolated by filtration. Purification was achieved by slurring in methanol (25 parts), followed by filtration to yield 3-phenyl-7-(4-amino-5-ethyl-3-methylphenyl)-2,6-dihydrobenzo[1:2-b, 4:5-b']-difuran. λmax=582 nm (Dichloromethane).

EXAMPLE 3

A mixture of glyoxylic acid 50% w/v (3.05 parts), water (20 parts) and methanol (10 parts) was stirred at ambient temperature. 2-ethylaniline (5.0 parts) was added and the mixture was stirred under reflux for 2 hours. After cooling to ambient temperature, the product was isolated by filtration, washed with a little water (50 parts) and dried to yield di(4-amino-3-ethylphenyl)acetic acid (5.5 parts).

EXAMPLE 4

A mixture of 5-hydroxy-2-oxo-3-phenyl-2,3-dihydrobenzofuran (3.8 parts), di(4-amino-3-ethylphenyl)acetic acid (5.0 parts) and 1,2-dichlorobenzene (30 parts) was stirred under reflux, under a stream of nitrogen for 96 hours. After cooling to 100° C., chloranil (1.5 parts) was added and the mixture was allowed to stir and cool to ambient temperature. Petroleum ether (30 parts) was added, the mixture was stirred for 1 hour and the product was isolated by filtration. Purification was achieved by column chromatography to yield 3-phenyl-7-(4-amino-3-ethylphenyl)-2,6-dihydrobenzo[1:2-b, 4:5-b']-difuran. λmax=568 nm (Chloroform).

EXAMPLE 5

A mixture of N-ethyl-2-methylaniline (10.0 parts) and methanol (30 parts) was stirred at ambient temperature. Glyoxylic acid 50% w/v (5.5 parts) was added and the mixture was stirred under reflux for 4 hours. After cooling in an ice bath the precipitated product was isolated by filtration, washed with methanol (20 parts) and dried to yield di(4-N-ethylamino-3-methylphenyl)-acetic acid (5.90 parts).

EXAMPLE 6

A mixture of 5-hydroxy-2-oxo-3-phenyl-2,3-dihydrobenzofuran (1.4 parts), di(4-N-ethylamino-3-methylphenyl)acetic acid (2.0 parts), 1,2-dichlorobenzene (20 parts) and dodecylbenzene sulphonic acid (0.53 parts) was stirred under reflux, under a stream of nitrogen for 22 hours. After cooling to ambient temperature, chloranil (1.5 parts) was added and the mixture was heated to 80° C. for 5 minutes. The mixture was cooled to ambient temperature, methanol (50 parts) was added and the mixture stirred at this temperature for 2 hours. The product was isolated by filtration to yield 3-phenyl-7-(4-N-ethylamino-3-methylphenyl)-2,6-dioxo-2,6-dihydrobenzo[1:2-b, 4:5-b']-difuran. λmax=620 nm (Dichloromethane).

EXAMPLE 7

A mixture of 2-methyl-6-tertiary butylaniline (10.0 parts), methanol (40.0 parts), and glyoxylic acid 50% w/v (4.54 parts) was stirred at ambient temperature for 44 hours. The precipitated product was isolated by filtration, washed with methanol (20 parts) and dried to yield di(4-amino-5-methyl-3-tertiarybutyl)acetic acid (6.9 parts).

EXAMPLE 8

A mixture of 5-hydroxy-2-oxo-3-phenyl-2,3-dihydrobenzofuran (3.79 parts), di(4-amino-5-methyl-3-tertiarybutylphenyl)acetic acid (6.4 parts) and 1,2-dichlorobenzene (60 parts) was stirred under reflux, under a stream of nitrogen for 24 hours. After cooling to 40° C., methanol (100 parts) was added, followed by chloranil (0.82 parts), and the mixture was stirred at 60° C. for 20 minutes. The mixture was allowed to stir and cool to room temperature. The product was isolated by filtration, washed twice with methanol (40 parts) and dried to yield 3-phenyl-7-(4-amino-5-methyl-3-tertiarybutylphenyl)-2,6-dioxo-2,6-dihydrobenzo[1:2-b, 4:5-b']-difuran. λmax=590 nm (Dichloromethane).

EXAMPLE 9

A mixture of 2,6-dimethylaniline (40 parts) and methanol (150 parts) was stirred at ambient temperature. Glyoxylic acid 50% w/v (24.5 parts) was added and the mixture was stirred for 24 hours at ambient temperature. The precipitated product was isolated by filtration, washed with methanol (30 parts) and dried to yield di(4-amino-3,5-dimethylphenyl)acetic acid (44.3 parts).

EXAMPLE 10

A mixture of 5-hydroxy-2-oxo-3-phenyl-2,3-dihydrobenzofuran (14.2 parts), di(4-amino-3,5-dimethylphenyl)acetic acid (17.97 parts) and 1,2-dichlorobenzene (150 parts) was stirred under reflux, under a stream of nitrogen for 24 hours. After cooling to 50° C., chloranil (2.7 parts) was added, followed by methanol (200 parts). The mixture was stirred at 50° C. for 30 minutes, and then allowed to stir and cool to ambient temperature. The product was isolated by filtration. Purification was achieved by recrystallisation from ethyl acetate (250 parts) to yield 3-phenyl-7-(4-amino-3,5-dimethylphenyl)-2,6-dioxo-2,6-dihydrobenzo[1:2-b, 4:5-b']-difuran (5.8 parts). λmax=590 nm (Dichloromethane).

EXAMPLE 11

The procedure of Example 3 was followed except that aniline (3.8 parts) was used in place of the 2-ethylaniline to yield di(4-aminophenyl)acetic acid.

EXAMPLE 12

The procedure of Example 2 was followed except that di(4-aminophenyl)acetic acid (3.7 parts) was used in place of the di(4-amino-5-ethyl-3-methylphenyl)acetic acid to yield 3-phenyl-7-(4-aminophenyl)-2,6-dioxo-2,6-dihydrobenzo[1:2-b, 4:5-b']difuran. λmax=605 nm.

EXAMPLE 13

The procedure of Example 3 was followed except that 2-methoxyaniline (5.1 parts) was used in place of the 2-ethylaniline to yield di(4-amino-3-methoxyphenyl)acetic acid.

EXAMPLE 14

The procedure of Example 2 was followed except that di(4-amino-3-methoxyphenyl)acetic acid (4.6 parts) was used in place of the di(4-amino-5-ethyl-3-methylphenyl)acetic acid to yield 3-phenyl-7-(4-amino-3-methoxyphenyl)-2,6-dioxo-2,6-dihydrobenzo[1:2-b, 4:5-b']difuran. λmax=600 nm.

EXAMPLE 15

The procedure of Example 3 was followed except that 2-chloroaniline (5.3 parts) was used in place of the 2-ethylaniline to yield di(4-amino-3-chlorophenyl)acetic acid.

EXAMPLE 16

The procedure of Example 2 was followed except that di(4-amino-3-chlorophenyl)acetic acid (4.8 parts) was used in place of the di(4-amino-5-ethyl-3-methylphenyl)acetic acid to yield 3-phenyl-7-(4-amino-3-chlorophenyl)-2,6-dioxo-2,6-dihydrobenzo[1:2-b, 4:5-b']difuran. λmax=570 nm.

EXAMPLE 17

The procedure of Example 3 was followed except that 2-(n-butyl)aniline (6.2 parts) was used in place of the 2-ethylaniline to yield di(4-amino-3-n-butylphenyl)acetic acid.

EXAMPLE 18

The procedure of Example 2 was followed except that di(4-amino-3-n-butylphenyl)acetic acid (5.4 parts) was used in place of the di(4-amino-5-ethyl-3-methylphenyl)acetic acid to yield 3-phenyl-7-(4-amino-3-n-butylphenyl)-2,6-dioxo-2,6-dihydrobenzo[1:2-b, 4:5-b']difuran. λmax=569 nm.

EXAMPLE 19

The procedure of Example 3 was followed except that N-ethyl-2-n-butylaniline (7.3 parts) was used in place of the 2-ethylaniline to yield di(4-(N-ethyl)amino-3-n-butylphenyl)acetic acid.

EXAMPLE 20

The procedure of Example 2 was followed except that di(4-(N-ethyl)amino-3-n-butylphenyl)acetic acid (6.3 parts) was used in place of the di(4-amino-5-ethyl-3-methylphenyl)acetic acid-to yield 3-phenyl-7-(4-(N-ethyl)amino-3-n-butylphenyl)-2,6-dioxo-2,6-dihydrobrnzo[1:2-b, 4:5-b']difuran. λmax=625 nm.

EXAMPLE 21

The procedure of Example 3 was followed except that N,N-diethylaniline (6.2 parts) was used in place of the 2-ethylaniline to yield di(4-(N,N-diethyl)aminophenyl)acetic acid.

EXAMPLE 22

The procedure of Example 2 was followed except that di(4-(N,N-diethyl)aminophenyl)acetic acid (5.4 parts) was used in place of the di(4-amino-5-ethyl-3-methylphenyl)acetic acid to yield 3-phenyl-7-(4-(N,N-diethyl)aminophenyl)-2,6-dioxo-2,6-dihydrobenzo-[1:2-b, 4:5-b']difuran. λmax=664 nm.

EXAMPLE 23

The procedure of Example 3 was followed except that N,N-dimethylaniline (5.0 parts) was used in place of the 2-ethylaniline to yield di(4-(N,N-dimethyl)aminophenyl)acetic acid.

EXAMPLE 24

The procedure of Example 2 was followed except that di(4-(N,N-dimethyl)aminophenyl)acetic acid (4.6 parts) was used in place of the di(4-amino-5-ethyl-3-methylphenyl)acetic acid to yield 3-phenyl-7-(4-(N,N-dimethyl)aminophenyl)-2,6-dioxo-2,6-dihydrobenzo[1:2-b, 4:5-b']difuran. λmax=650 nm.

EXAMPLE 25

The procedure of Example 4 was followed except that 5-hydroxy-2-oxo-3-(4-n-propoxyphenyl)-2,3-dihydrobenzofuran (3.9 parts) was used in place of the 5-hydroxy-2-oxo-3-phenyl-2,3-dihydrobenzofuran to yield 3-(4-n-propoxyphenyl)-7-(4-amino-3-ethylphenyl)-2,6-dioxo-2,6-dihydrobenzo[1:2-b, 4:5-b']difuran. $\lambda_{max}$=574 nm.

EXAMPLE 26

The procedure of Example 2 was followed except that 5-hydroxy-2-oxo-3-(4-n-propoxyphenyl)-2,3-dihydrobenzofuran (3.9 parts) was used in place of the 5-hydroxy-2-oxo-3-phenyl-2,3-dihydrobenzofuran to yield 3-(4-n-propoxyphenyl)-7-(4-amino-3-ethyl-5-methylphenyl)-2,6-dioxo-2,6-dihydrobenzo[1:2-b, 4:5-b']difuran. $\lambda_{max}$=586 nm.

EXAMPLE 27

The procedure of Example 2 was followed except that 5-hydroxy-2-oxo-3-(4-propoxyphenyl)-2,3-dihydrobenzofuran (3.9 parts) was used in place of the 5-hydroxy-2-oxo-3-phenyl-2,3-dihydrobenzofuran to yield; 3-(4-hydroxyphenyl)-7-(4-amino-3-ethyl-5-methylphenyl)-2,6-dioxo-2,6-dihydrobenzo [1:2-b, 4:5-b']difuran. $\lambda_{max}$=580 nm.

EXAMPLE 28

The procedure of Example 2 was followed except that 5-hydroxy-2-oxo-3-(3-ethyl-4-hydroxyphenyl)-2,3-dihydrobenzofuran (4.2 parts) was used in place of the 5-hydroxy-2-oxo-3-phenyl-2,3-dihydrobenzofuran to yield 3-(3-ethyl-4-hydroxyphenyl)-7-(4-amino-3-ethyl-5-methylphenyl)-2,6-dioxo-2,6-dihydrobenzo [1:2-b, 4:5-b']difuran. $\lambda_{max}$=584 nm.

EXAMPLE 29

The procedure of Example 4 was followed except that 5-hydroxy-2-oxo-3-(4-methylphenyl)-2,3-dihydrobenzofuran (3.7 parts) was used in place of the 5-hydroxy-2-oxo-3-phenyl-2,3-dihydrobenzofuran to yield 3-(4-methylphenyl)-7-(4-amino-3-ethylphenyl)-2,6-dioxo-2,6-dihydrobenzo [1:2-b, 4:5-b']difuran. $\lambda_{max}$=566 nm.

EXAMPLE 30

The procedure of Example 4 was followed except that 5-hydroxy-2-oxo-3-(4-ethylphenyl)-2,3-dihydrobenzofuran (4.0 parts) was used in place of the 5- hydroxy-2-oxo-3-phenyl-2,3-dihydrobenzofuran to yield 3-(4-ethylphenyl)-7-(4-amino-3-ethylphenyl)-2,6-dioxo-2,6-dihydrobenzo [1:2-b, 4:5-b']difuran. $\lambda_{max}$=568 nm.

EXAMPLE 31

The procedure of Example 4 was followed except that 5-hydroxy-2-oxo-3-(4-isopropylphenyl)-2,3-dihydrobenzofuran (4.2 parts) was used in place of the 5-hydroxy-2-oxo-3-phenyl-2,3-dihydrobenzofuran to yield 3-(4-isopropylphenyl)-7-(4-amino-3-ethylphenyl)-2,6-dioxo-2,6-dihydrobenzo [1:2-b, 4:5-b']difuran. $\lambda_{max}$=568 nm.

EXAMPLE 32

The procedure of Example 2 was followed except that 5-hydroxy-2-oxo-3-(4-methoxyphenyl)-2,3-dihydrobenzofuran (4.0 parts) was used in place of the 5-hydroxy-2-oxo-3-phenyl-2,3-dihydrobenzofuran to yield 3-(4-methoxyphenyl)-7-(4-amino-3-ethyl-5-methylphenyl)-2,6-dioxo-2,6-dihydrobenzo [1:2-b, 4:5-b']difuran. $\lambda_{max}$=584 nm.

EXAMPLE 33

The procedure of Example 4 was followed except that 5-hydroxy-2-oxo-3-(5-isopropoxyphenyl)-2,3-dihydrobenzofuran (4.4 parts) was used in place of the 5-hydroxy-2-oxo-3-phenyl-2,3-dihydrobenzofuran to yield 3-(4-isopropoxyphenyl)-7-(4-amino-3-ethylphenyl)-2,6-dioxo-2,6-dihydrobenzo [1:2-b, 4:5-b']difuran. $\lambda_{max}$=576 nm.

EXAMPLE 34

The procedure of Example 2 was followed except that 5-hydroxy-2-oxo-3-(4-fluorophenyl)-2,3-dihydrobenzofuran (3.8 parts) was used in place of the 5-hydroxy-2-oxo-3-phenyl-2,3-dihydrobenzofuran to yield 3-(4-fluorophenyl)-7-(4-amino-3-ethyl-5-methylphenyl)-2,6-dioxo-2,6-dihydrobenzo [1:2-b, 4:5-b']difuran. $\lambda_{max}$=584 nm.

EXAMPLE 35

The procedure of Example 2 was followed except that 5-hydroxy-2-oxo-3-(4-hydroxy-3,5-dimethylphenyl)-2,3-dihydrobenzofuran (4.0 parts) was used in place of the 5-hydroxy-2-oxo-3-phenyl-2,3-dihydrobenzofuran to yield 3-(4-hydroxy-3,5-dimethylphenyl)-7-(4-amino-3-ethyl-5-methylphenyl)-2,6-dioxo-2,6-dihydrobenzo [1:2-b, 4:5-b']difuran. $\lambda_{max}$=584 nm.

We claim:

1. A process for the preparation of a substituted acetic acid of the Formula (2):

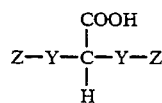

Formula 2 wherein:

Y is a radical of the formula (4):

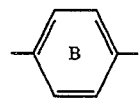

Formula 4 or a radical of the formula (5):

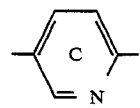

Formula 5 or a radical of the formula (6):

Formula 6 wherein

Ring B is unsubstituted or is substituted by from one to four further groups;

Ring C is unsubstituted or is substituted by from one to three further groups;

Ring D is unsubstituted or is substituted by one or two further groups;

Z is —NR$^1$R$^2$;

R$^1$ and R$^2$ are each independently H or are independently selected from optionally substituted alkyl, alkenyl, cycloalkyl, aralkyl, aryl and heteroaryl; or R$^1$ and R$^2$ together with the nitrogen atom to which they are attached form a piperidino or morpholino ring; or R$^1$ and R$^2$ each independently together with the nitrogen to which they are attached and the adjacent carbon atom of Ring B form a tetrahydroquinolino or julolidino ring;

by reacting a compound of the Formula (7):

Formula 7 with glyoxylic acid.

* * * * *